United States Patent [19]

Saltzman

[11] 4,014,908

[45] Mar. 29, 1977

[54] CHEMICAL PROCESS

[75] Inventor: William H. Saltzman, New Rochelle, N.Y.

[73] Assignee: Intellectual Property Development Corporation, New Rochelle, N.Y.

[22] Filed: Feb. 20, 1976

[21] Appl. No.: 660,037

Related U.S. Application Data

[63] Continuation-in-part of Ser. No. 474,735, May 30, 1974, abandoned, which is a continuation of Ser. No. 467,710, May 7, 1974, abandoned, and a continuation-in-part of Ser. No. 417,170, Nov. 19, 1973, Pat. No. 3,919,266, and a continuation-in-part of Ser. No. 290,910, Sept. 21, 1972, abandoned.

[52] U.S. Cl. .............................................. 260/397.1

[51] Int. Cl.² .......................................... C07J 9/00
[58] Field of Search ................................... 260/397.1

[56] References Cited

UNITED STATES PATENTS 3,833,620   9/1974   Saltzman ..................... 260/397.1

*Primary Examiner*—Elhert L. Roberts

[57] ABSTRACT

This invention relates to new and novel methods for the production of substantially pure bile acids, and particularly, 3α, 7α-dihydroxy-5β-cholanic acid, from natural sources thereof.

19 Claims, No Drawings

CHEMICAL PROCESS

This Application is a continuation in part application of my previously filed, copending application, Ser. No. 474,735, filed May 30, 1974 now abandoned which in turn is a continuation of prior filed application Ser. No. 467,710, filed May 7, 1974 abandoned and is a continuation-in-part application of my previously filed, application Ser. No. 417,170, filed Nov. 19, 1973 now U.S. Pat. No. 3,919,266; both of which are continuation in part applications of my previously filed application, Ser. No. 290,910, filed Sept. 21, 1972 now abandoned. More particularly, this invention relates to new and novel methods for producing substantially pure bile acids, and particularly $3\alpha, 7\alpha$-dihydroxy-$5\beta$cholanic acid, from natural animal sources thereof.

This invention relates to and has as its object, the production of substantially pure bile acids from natural sources thereof, and to new and useful processes therefore.

Even more particularly, this invention relates to a method of producing substantially pure $3\alpha, 7\alpha$-dihydroxy-$5\alpha$-cholanic acid, either directly from natural animal sources thereof, or by the purification of rather impure forms of said bile acid. By the term "substantially pure" in this Specification and the Claims appended hereto, it is meant to denote a chemical purity in excess of 99.0%, as evidenced by standard and acceptable analytical procedures. Heretofore, the bile acid, $3\alpha, 7\alpha$-dihydroxy-$5\beta$-cholanic acid, has been produced either by direct isolation and purification from natural animal sources, or by synthetic methods employing such starting materials as $3\alpha, 7\alpha, 12\alpha$-trihydroxy-$5\beta$-cholanic acid. Methods for the direct isolation and purification of $3\alpha, 7\alpha$-dihydroxy-$5\beta$-cholanic acid from natural animal sources are described in my prior filed applications, Ser. Nos. 417,170 and 290,910 filed Nov. 19, 1973 and Sept. 21, 1972 respectively.

A method for the synthetic production of $3\alpha, 7\alpha$-dihydroxy-$5\beta$-cholanic acid has been described by both Feiser, et al in J. Amer. Chem. Soc., 72:5530 (1950) and Hofmann, Acta Chem. Scand., 17:173 (1963). Although the methods heretofore employed provide a final product of adequate purity, it was felt that it would be most desirable to obtain the purest final product possible, especially in view of the final therapeutic use to which the compound was to be put. Recently, it was discovered that the final compound of this invention possessed very valuable therapeutic properties, in that it was found to be capable of non-surgically dissolving cholesterol gallstones in humans. For this purpose it was orally administered to patients over extended periods of time until their gallstones were dissolved. In view of the fact that relatively high daily dosage amounts of the compound, i.e., 750 to 1000 mg. per day, have to be administered to the patients, it is considered desirable that the purest form thereof be produced for this purpose. Therefore, efforts were made to prepare the purest form of the compound.

In 1963, Hofmann reported the existence of $3\alpha, 7\alpha$-dihydroxy-$5\beta$-cholanic acid, in the form of needle-like crystals having a melting point of 119° C., and taught to be pure $3\alpha, 7\alpha$-dihydroxy-$5\beta$-cholanic acid. In addition, the Merck Index, 8th Edition, at page 229 also reports that the pure compound has a melting point of 119° C. However, until now, these appear to be the only reports of the existence of this needle-like crystal form of $3\alpha, 7\alpha$-dihydroxy-$5\beta$-cholanic acid, and no one has apparently been able to reproduce the reported findings or the needle-like crystals. It has now been found possible to produce $3\alpha, 7\alpha$-dihydroxy-$5\beta$-cholanic acid in the form of needle-like crystals having a melting point of 119° C., by the practice of this invention, It has been found possible to produce the needle-like crystals of $3\alpha, 7\alpha$-dihydroxy-$5\beta$-cholanic acid by further purifying the $3\alpha, 7\alpha$-dihydroxy-$5\beta$-cholanic acid final product produced in accordance with the procedures set forth in my previous application Ser. No. 417,170. In addition, it has also been found possible to produce these needle-like crystals by precisely following the procedures taught by Hofmann, provided that the starting material was relatively pure, for example, that produced in accordance with the procedures set forth in my application Ser. No. 417,170.

Upon producing the needle-like crystal form of $3\alpha, 7\alpha$-dihydroxy-$5\beta$-cholanic acid, this material was subjected to thorough analysis to confirm the fact that it represented the pure form of the compound as had been previously reported. Upon chromatographic analyses, i.e., TLC and GLC for bile acids, it was found that the needle-like crystalline material did appear to be essentially pure $3\alpha, 7\alpha$-dihydroxy-$5\beta$-cholanic acid. However, upon further analysis, such as, elemental analysis for C; H; and O; acid titration; and infra red spectrum, results were obtained which unexpectedly were at considerable variance with those anticipated for a pure product. The elemental analysis indicated the presence of an excess amount of C and H; the neutralization equivalent showed that the acid content fell significantly below the level anticipated for a pure product; and upon careful examination, the infrared spectrum contained various peaks which indicated the presence of an impure product. In view of these findings, it was concluded that contrary to the previous reports, the needle-like crystalline form of $3\alpha, 7\alpha$-dihydroxy-$5\beta$-cholanic acid was not a pure form of the compound, but was the result of some physio-chemical alteration of the compound molecule which resulted in the formation of a complex of the bile acid and the organic solvent of crystallization, which was encaptured therein as an inclusion compound. This was totally an unexpected discovery, since it had always been taught and assumed that the crystallization procedures and solvent systems heretofore employed to produce the compound, i.e. ethyl acetate-heptane, resulted in no reactive process between the compound and the organic solvents. In fact, this assumption of non-reactivity was the main reason for employing the solvent systems, such as ethyl acetate-heptane or ethyl acetate-hexane, for the crystallization of the $3\alpha, 7\alpha$dihydroxy-$5\beta$-cholanic acid.

In order to actually confirm that this inclusion complex of the $3\alpha, 7\alpha$-dihydroxy-$5\beta$-cholanic acid and the organic solvent was actually formed, further experimentation was performed. Initially the needle-like crystals were thoroughly dried, i.e. drying in an oil-pump vacuum oven at 2 mm. Hg at between 90° and 100° C for 96 hours, to remove residual solvents. A measured amount of this dried crystalline material was then redissolved in ethyl acetate and recrystallized by use of seed crystals with a premeasured amount of 14-C labeled heptane. The resultant crystalline material was then isolated and thoroughly dried. This dried recrystallized crystalline material was then analyzed in a scintillation counter to determine the amount of residual radioactivity. The results, obtained, i.e., a relatively high radioactivity count, can only be explained by the fact that the resultant needle-like crystalline product was actually an inclusion complex, wherein the heptane was encaptured within the crystalline structure as the included compound. The bile acid molecules were apparently altered physically in some manner to include the heptane within the crystals. It was further determined that for every four molecules of the bile acid, about one molecule of heptane was included within the crystals as the included compound.

Obviously, in view of the inclusion complex character of this product, it would not be possible to employ the crystals for pharmaceutical uses. This was true even though the crystalline material was essentially pure except for the included organic solvent. Therefore, it became most desirable to retain the crystalline product's purity with the elimination of the solvent, i.e., heptane, because of its extremely pure character. Further work demonstrated that the crystallization procedure whereby the needle-like crystals were produced actually aided in the purification of the final product by preventing, inhibiting or excluding from the crystals the presence of undesired impurities, such as lithocholic acid, a known hepatoxin and cholic acid. It was also found that crystallization apparently does not occur spontaneously in the presence of two or more percent of impurities. Furthermore, it has also been found that the speed of the crystallization process appears to effect the relative purity of the final product obtained. The slower the rate of crystal growth, the purer the product. The speed of the crystal growth process appears to be controllable by the rate of cooling of the crystallization solution during the period of crystal growth. It has been found to be most preferable to initiate the crystal growth process at elevated temperatures, i.e., 70° to 85° C., and then during the period of crystal growth, allow to cool slowly to room temperature and then further cool to about 4° C., until crystal growth is completed. The slower the rate of cooling to room temperature, the slower the rate of crystal growth, and the purer the resultant crystalline product.

There has now been found a method whereby a substantially pure $3\alpha,7\alpha$-dihydroxy-$5\beta$-cholanic acid product, derived from the inclusion complex of $3\alpha,7\alpha$-dihydroxy-$5\beta$-cholanic acid and an organic solvent of crystallization, and free of said organic solvent, can be produced. This method of purification involves the further treatment of the $3\alpha,7\alpha$-dihydroxy-$5\beta$-cholanic acid-organic solvent inclusion complex crystals to eliminate the organic solvent and yield only the resultant substantially pure $3\alpha,7\alpha$-dihydroxy-$5\beta$-cholanic acid. Notwithstanding the fact that the crystallization solvent system of choice in the production of $3\alpha,7\alpha$-dihydroxy-$5\beta$-cholanic acid is ethyl acetate-heptane, other solvent systems have been employed with apparently the same inclusion complex crystals being produced. Thus, it has been found that ethyl acetate alone yields an inclusion complex with ethyl acetate as the included compound. An ethyl acetate hexane solvent system provides an inclusion complex with hexane as the included compound.

To remove the undesired included organic solvent from the crystalline inclusion complex, one method has been found which involves the further treatment of the crystalline inclusion complex. The crystal inclusion complex is first treated with a base, for example, an alkali metal base such as KOH, NaOH or $NH_4OH$, until there is a complete dissolution of the crystals in the basic solution. It has been found that complete dissolution is usually obtained when the pH of the resultant solution reaches between 9 to 11 and preferably when the pH is about 10. The resultant solution is then treated with a mineral acid, for example, $H_2SO_4$ or HCl to bring the pH to between 1 and 3, and preferably to about 2.0. The resultant acidified solution is then filtered and the resultant cake very thoroughly washed with water to yield the pure, solvent free, $3\alpha,7\alpha$-dihydroxy-$5\beta$-cholanic acid, which is then thoroughly dried to give the final substantially pure, solvent-free, $3\alpha,7\alpha$-dihydroxy-$5\beta$-cholanic acid, which may then be directly employed for use in the therapeutic treatment of human beings.

An alternative method that has also been found to obtain the substantially pure solvent-free final product of this invention. This alternative method involves the crystallization of the $3\alpha,7\alpha$-dihydroxy-$5\beta$-cholanic acid product to yield the needle-like crystalline inclusion complex in a solvent system comprised of ethyl acetate-cycloalkane. Among the cycloalkane compounds which may be employed herein are included cyclohexane, cycloheptane and cyclopentane. The resultant needle-like crystals are an inclusion complex comprised of $3\alpha,7\alpha$-dihydroxy-$5\beta$-cholanic acid and the cycloalkane included compound. The resultant inclusion complex needlelike crystals containing the cycloalkane included compound are then subjected to sufficient drying conditions to remove the cycloalkane included compound. It appears that these cycloalkane clathrate are susceptable to removal by drying the crystals in an oil pump vacuum at a pressure of 2 mm. Hg. at a temperature of 90° C. for a period of about 96 hours to yield the substantially pure, solvent free $3\alpha,7\alpha$-dihydroxy-$5\beta$-cholanic acid final product of this invention. In addition, it has also been found that a $3\alpha,7\alpha$-dihydroxy-$5\beta$-cholanic acid-ethyl acetate inclusion complex may also be treated in the foregoing manner.

In addition to the foregoing, a further method has been found to yield the solvent free final product of this invention. This additional method involves the dissolution of the inclusion complex needle-like crystals of $3\alpha,7\alpha$-dihydroxy-$5\beta$-cholanic acid and the organic solvent of crystallization in an alcohol, for example, methanol or ethanol and then evaporating the resulting solution to dryness to obtain the substantially pure, organic solvent-free $3\alpha,7\alpha$-dihydroxy-$5\beta$-cholanic acid of the final product of the instant invention.

The instant invention may be further illustrated by the following examples:

EXAMPLE I

Twenty grams of the final product obtained in accordance with the procedures set forth in U.S. Pat. No. 3,931,256, are dissolved, with stirring, in 500 ml of hot ethyl acetate maintained at a temperature of 75°–85° C. The resultant solution while still hot, is then filtered and the resultant filtrate is held at a temperature of 60° C. with stirring. To this stirred solution is slowly added, with stirring, 300 ml of n-heptane, and the resultant solution is allowed to slowly cool to room temperature. Within a few minutes, rosettes of needle-like crystals can be seen to begin to form. The resultant crystals are permitted to grow for four hours at room temperature and then are refrigerated at about 4 C. overnight until crystal growth is completed. The resultant crystals are then recovered and dried for 96 hours in an oil pump vacuum oven at 2 mm. Hg at a temperature of 85° C.

The final crystalline product was found to have a m.p. of 119° C.

EXAMPLE II

Twenty grams of the final product obtained in accordance with the procedures of U.S. Pat. No. 3,931,256, are treated in accordance with the teachings and procedures set forth by Hofmann, Acta Chem. Scand. 17:173 (1963) to yield the needlelike crystals of 3α, 7α-dihydroxy-5β-cholanic acid having a melting point of 119° C.

EXAMPLE III

Twenty grams of the final product obtained in accordance with the procedures set forth in U.S. Pat. No. 3,931,256 are dissolved with stirring, in 500 ml of ethyl acetate maintained at a temperature of 75°–85° C. The resultant solution while still hot, was then filtered twice and the resultant filtrate was held at a temperature at 85° C. with stirring. The ethyl acetate was allowed to evaporate and upon evaporation of a portion of the ethyl acetate rosettes of needlelike crystals began to appear. The resultant crystal containing solution was then allowed to cool to room temperature and was then refrigerated until crystal growth was complete. The crystals were recovered and dried, yielding a crystalline product having a melting point of 117°–119° C.

EXAMPLE IV

The products obtained in Examples I, II, III were subjected to GLC analysis revealing that the crystalline products were inclusion complexes of 3α,7α-dihydroxy-5β-cholanic acid having heptane, heptane and ethyl acetate clathrates, respectively, in amounts in excess of 5%.

EXAMPLE V

Five grams of the crystalline product obtained in Example II were dissolved in 125 ml. of warm methanol with stirring. Stirring of the resultant solution was maintained for 30 minutes. The temperature of the solution was raised to cause evaporation of the methanol. The solution was evaporated to dryness yielding a dry white powder which on TLC and GLC analysis was found to be solvent free 3α, 7α-dihydroxy-5β-cholanic acid having a melting point of 143°–145° C.

EXAMPLE VI

Twenty grams of the crystalline product obtained in accordance with the procedure of Example II was dissolved in a 25% NH$_4$OH solution until all solids were dissolved and the pH reached 10.0. The resultant solution, pH 10.0 was then cooled, filtered and treated with 2N HCl at 25 C. until the pH of the resultant solution reached 2.0. The resultant reaction mixture was then filtered and the resultant cake washed 3 times with 500 ml. of water, and then dried overnight in an oil pump vacuum oven at 2 mm. Hg at a temperature of 85° C.

The resultant dried product was found to have an initial melting point of 108°–115° C., at which point it entered into a glass-like state, which had a final melting point of from about 140°–145° C. A small portion of the dried material was then dissolved in ethyl acetate and the resulting solution had a slightly turbid appearance, indicating the presence of undesired impurities, which apparently were present because of incomplete water washing of the product. The dried material was then subjected to vigorous and thorough water washing to yield a final product, which after drying for 24 hours in an oil pump vacuum oven at 85° C. had a melting point of from 142°–145° C.

In addition, analyses by TLC and GLC disclosed that the product was substantially pure 3α,7α-dihydroxy-5β-cholanic acid, free of any residual organic solvent, i.e., heptane or ethyl acetate.

EXAMPLE VII

Twenty grams of the final product of Example III were dissolved in 500 ml of ethyl acetate and held with stirring for 30 minutes at 70° C. To this solution was added slowly, 300 ml. of cyclohexane and the resultant solution allowed to cool to room temperature. Within minutes, rosettes of needlelike crystals began to form. The reaction mixture was allowed to cool until crystal growth was complete. The crystals were recovered and air dried. The air dried crystals were subjected to TLC and GLC analyses which showed the presence of cyclohexane as an inclusion compound. The inclusion complex crystals were then subjected to drying in an oil pump vacuum oven at 2 mm Hg overnight at a temperature of 85° C. The resultant dried product were then subjected to TLC and GLC analyses which showed the product to be substantially pure 3α, 7α-dihydroxy-5β-cholanic acid, free of solvent and having a melting point of 142°–145° C.

In addition to the foregoing, the instant invention may be practiced in those cases wherein the source of the neelde-like crystalline inclusion complex is obtained from material obtained from 3α, 7α-dihydroxy-5β-cholanic acid prepared in accordance with the synthtic procedures set forth in Hofmann, Acta Chem. Scand. 17;173 (1963).

The final products of this invention are useful in the therapeutic treatment of patients for the dissolution of cholesterol gallstones. To achieve these purposes, the final products of this invention may be orally administered to the patient being treated in such final dosage forms as may be usually and satisfactorily employed for such purposes. The dosage forms employed may contain such pharmaceutically acceptable, non-toxic inert carriers usually employed for such purposes. Thus, such final dosage forms, employing the pharmaceutically acceptable carriers, as tablets, capsules, elixirs, solutions, suspensions, and the like may be employed in the practice of this invention. Most preferably, capsule and tablet final dosage forms may be employed in the oral administration of this final products of this invention to the patients being treated.

The invention may be variously otherwise embodied within the scope of the appended claims.

What is claimed is:

1. The method of obtaining organic solvent free 3α, 7α-dihydroxy - 5β - cholanic acid from a clathrate consisting of a needle like, crystalline inclusion complex of 3α, 7α-dihydroxy - 5β -cholanic acid and an organic solvent of crystallization included compound, which method comprises:
   a. Treating the said clathrate with an alkali metal base to obtain complete dissolution of said clathrate and to yield a solution having a pH of from about 9 to 11;
   b. Treating said resultant solution with a mineral acid to yield a solution having a pH of from about 1 to 3; and
   c. Recovering the resultant organic solvent-free 3α, 7α- dihydroxy - 5β-cholanic acid, 2. The method of claim 1, wherein in step a, the alkali metal base is KOH, NaOH or NH₄OH.

3. The method of claim 1, wherein in step b, the mineral acid is $H_2SO_4$ or HCl.

4. The method of obtaining organic solvent free $3\alpha$, $7\alpha$- dihydroxy - $5\beta$ - cholanic acid from a clathrate consisting of a needle-like, crystalline inclusion complex of $3\alpha$, $7\alpha$ -dihydroxy - $5\beta$ - cholanic acid and an organic solvent of crystallization as the included compound, which method comprises subjecting the said inclusion complex to drying at an elevated temperature under reduced pressure over an extended period of time.

5. The method of claim 4 wherein the organic solvent of crystallization is a cycloalkane or ethyl acetate.

6. The method of claim 4, wherein the elevated temperature is about 90° C., the reduced pressure is about 2 mm of Hg., and the drying period is about 96 hours.

7. The method of obtaining organic solvent-free $3\alpha$, $7\alpha$- dihydroxy - $5\beta$ - cholanic acid from a clathrate consisting of a needle-like crystalline inclusion complex of $3\alpha,7\alpha$- hydroxy - $5\beta$ cholanic acid and an organic solvent of crystallization as the included compound, which method comprises:
   a. Dissolving said clathrate in an alcohol; and
   b. Evaporating off the said alcohol to yield solvent-free $3\alpha$, $7\alpha$-dihydroxy - $5\beta$-cholanic acid.

8. The method of claim 7 wherein the alcohol is methanol or ethanol.

9. The method of obtaining solvent-free $3\alpha$, $7\alpha$-dihydroxy - $5\beta$- cholanic acid, which comprises:
   a. Obtaining a clathrate consisting of a needle-like crystalline inclusion complex of $3\alpha$, $7\alpha$-dihydroxy-$5\beta$-cholanic acid and an organic solvent of crystallization thereof as the included compound;
   b. Removing from said clathrate the said organic solvent included compound; and
   c. Recovering the resultant solvent-free $3\alpha$, $7\alpha$-dihydroxy- $5\beta$-cholanic acid.

10. The method of claim 9, wherein the clathrate has a melting point of about 119° C.

11. The method of claim 9, wherein in step a, the organic solvent included compound is selected from the group consisting of ethyl acetate, heptane, hexane, cyclopentane, cyclohexane and cycloheptane.

12. The method of obtaining solvent-free $3\alpha,7\alpha$-dihydroxy-$5\beta$-cholanic acid, which comprises:
   a. Obtaining a clathrate consisting of a needle-like crystalline inclusion complex of $3\alpha$, $7\alpha$-dihydroxy-$5\beta$-cholanic acid and an organic solvent selected from the group consisting of, hexane, and heptane, as the included compound;
   b. Removing from said clathrate the said organic solvent included compound; and
   c. Recovering the resultant solvent-free $3\alpha$, $7\alpha$-dihydroxy - $5\beta$ - cholanic acid.

13. The method of obtaining solvent-free $3\alpha$, $7\alpha$-dihydroxy - $5\beta$- cholanic acid, which comprises:
   a. Obtaining a clathrate consisting of a needle-like crystalline inclusion complex of $3\alpha$, $7\alpha$-dihydroxy -$5\beta$- cholanic acid and a cycloalkane as the included compound;
   b. Removing the cycloalkane included compound from said clathrate by subjecting said clathrate to drying in a vacuum at an elevated temperature over an extended period of time; and
   c. Recovering the resultant solvent-free $3\alpha$, $7\alpha$ - dihydroxy - $5\beta$- cholanic acid.

14. The method of claim 12 wherein in step a, the organic solvent included compound is heptane.

15. The method claim 12, wherein in step a, the organic solvent included compound is hexane.

16. The method of claim 9, wherein in step a, the organic solvent included compound is ethyl acetate.

17. The method of claim 9, wherein in step a, the organic solvent included compound is heptane.

18. The method of claim 9, wherein in step a, the organic solvent included compound is hexane.

19. The method of claim 4, wherein the organic solvent of crystallization is selected from the group consisting of ethyl acetate, hexane, heptane, cyclopentane, cyclohexane and cycloheptane.

* * * * *